United States Patent [19]

Wolf et al.

[11] Patent Number: 5,082,845
[45] Date of Patent: Jan. 21, 1992

[54] THERAPEUTIC XANTHINE DERIVATIVES FOR THE TREATMENT OF PEPTIC ULCER DISEASE

[75] Inventors: Erhard Wolf, Hofheim am Taunus; Ulrich Gebert; Harald Furrer, both of Kelkheim, all of Fed. Rep. of Germany; Toshizo Tanaka; Masao Sakurai, both of Saitama, Japan; Masayoshi Goto, Kanagawa, Japan

[73] Assignee: Hoechst Japan Limited, Tokyo, Japan

[21] Appl. No.: 311,910

[22] Filed: Feb. 17, 1989

[30] Foreign Application Priority Data

Feb. 19, 1988 [JP] Japan .................................. 63-35484

[51] Int. Cl.$^5$ ..................... A61K 31/52; C07D 473/06
[52] U.S. Cl. .................................. 514/263; 544/267; 544/271
[58] Field of Search ................ 544/267, 271; 514/263, 514/264

[56] References Cited

U.S. PATENT DOCUMENTS

| | | | |
|---|---|---|---|
| 4,207,321 | 6/1980 | Furrer et al. | 544/267 X |
| 4,242,345 | 12/1980 | Brenner et al. | 514/263 |
| 4,372,959 | 2/1983 | Goring | 544/271 |
| 4,616,020 | 10/1986 | Furrer et al. | 514/264 |
| 4,636,507 | 1/1987 | Kreutzer et al. | 514/263 |
| 4,657,910 | 4/1987 | Morgan | 514/263 |
| 4,713,455 | 12/1987 | Furrer et al. | 544/267 |
| 4,772,607 | 9/1988 | Badger et al. | 514/263 |
| 4,833,146 | 5/1989 | Gebert et al. | 514/263 |
| 4,845,102 | 7/1989 | Sakurai et al. | 514/263 |
| 4,880,791 | 11/1989 | Weisthmann et al. | 514/161 |

FOREIGN PATENT DOCUMENTS

| | | |
|---|---|---|
| 0042706 | 12/1981 | European Pat. Off. . |
| 0232438 | 8/1987 | European Pat. Off. . |
| 0266559 | 5/1988 | European Pat. Off. . |
| 0330031 | 8/1989 | European Pat. Off. . |
| 2432702 | 1/1976 | Fed. Rep. of Germany . |

OTHER PUBLICATIONS

Terapevticeskij Archiv, vol. 57, No. 2, 1985, pp. 52-55, Moskva; L. P. Vorobyov et al.: "Clinico-functional Evaluation of the Efficacy of Trental in the Treatment of Peptic Ulcer of the Duodenum" and English Abstract.

Frisius et al., Chemical Abstracts, vol. 87, No. 9 (1977), Abstract No. 62749f.

Hinze, Chemical Abstracts, vol. 78, No. 5 (1973), Abstract 23834z.

Hoechst AG, Chemical Abstract, vol. 94, No. 5 (1981), Abstract 30794v.

Primary Examiner—Diana G. Rivers
Attorney, Agent, or Firm—Finnegan, Henderson, Farabow, Garrett, and Dunner

[57] ABSTRACT

Therapeutic agents for the treatment of peptic ulcer disease, containing as active ingredient, at least one compound of the general formula

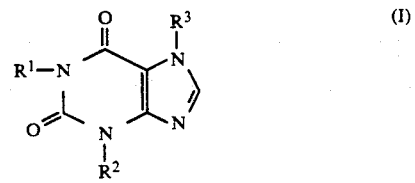

wherein $R^1$ and $R^3$ are the same or different and are each $(C_1-C_8)$alkyl,

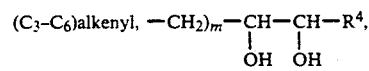

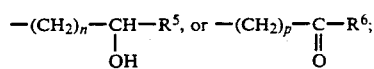

$R^2$ is $(C_1-C_4)$alkyl; $R^4$ and $R^5$ are the same or different and are each hydrogen or $(C_1-C_2)$alkyl; $R^6$ is $(C_1-C_2)$alkyl; and m, n and p are the same or different and are each 1, 2, 3, 4, 5 or 6; with the proviso that one of the groups $R^1$ and $R^3$ is

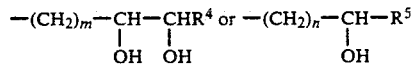

or that $R^3$ represents

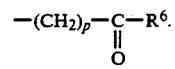

Some of the compounds of formula I are novel.

8 Claims, No Drawings

THERAPEUTIC XANTHINE DERIVATIVES FOR THE TREATMENT OF PEPTIC ULCER DISEASE

BACKGROUND OF THE INVENTION (1) Field of the Invention

This invention relates to pharmaceuticals suitable for use in the treatment of peptic ulcer disease. Peptic ulcer is an ulceration of the mucous membrane of the stomach and/or duodenum; the mucous membrane is damaged by the action of hydrochloric acid and pepsin due to its decreased resistance to the aggressive factors induced by various causes including physical and psychological stress.

(2) Problems to Be Solved by the Invention

Until recently, sodium bicarbonate and aluminum compounds had been used to neutralize gastric acid as aggressive factor. The drugs commonly used now to treat peptic ulcer disease include anticholinergics, gastro-protective agents, drugs improving mucosal blood flow, and $H_2$-receptor antagonists.

Drugs for peptic ulcers are administered for a long period of time and are required to have the fewest adverse effects as well as high efficacy. However, the available drugs are not necessarily satisfactory in safety and efficacy. In addition there is another problem associated with the use of the drugs, namely, the relapse of ulcer after drug treatment is stopped. For example, the $H_2$-receptor antagonists are very effective in improving gastric and duodenal ulcers by inhibiting gastric acid secretion but ulcers recur at high incidence after discontinuing treatment with the drugs.

As a result of our extensive studies for superior therapeutics for peptic ulcer disease, we have found that specific xanthine derivatives have high efficacy and safety enough to be new drugs suitable for use in the treatment of the disease, inclusive of irritations of the gastro-intestinal mucosa produced by drugs such as nonsteroidal antiinflammatory agents.

DETAILED DESCRIPTION OF THE INVENTION

Thus, the present invention provides therapeutic agents for the treatment of peptic ulcer disease containing, as active ingredient, at least one compound of the general formula I

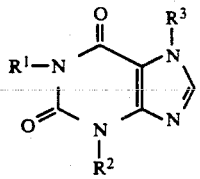

wherein $R^1$ and $R^3$ are the same or different and are each $(C_1-C_8)$alkyl, $(C_3-C_6)$alkenyl,

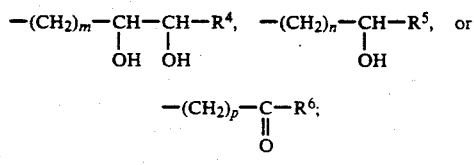

$R^2$ is $(C_1-C_4)$alkyl; $R^4$ and $R^5$ are the same or different and are each hydrogen or $(C_1-C_2)$alkyl; $R^6$ is $(C_1-C_2)$alkyl; and m, n, and p are the same or different and are each 1, 2, 3, 4, 5, or 6; with the proviso that one of the groups $R^1$ and $R^3$ is

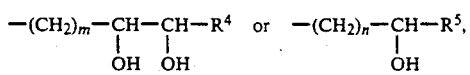

or that $R^3$ represents

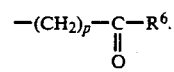

In this context, those therapeutic agents are preferred which contain at least one compound of the formula I in which $R^1$ and $R^3$ denote a straight-chain or branched alkyl group having up to 6 C atoms, allyl, ($\omega$, $\omega$-1)- or ($\omega$-1, $\omega$-2)-dihydroxyalkyl having 4 to 7 C atoms, ($\omega$-1)-hydroxy- or ($\omega$-1)-oxoalkyl having each 3 to 6 C atoms; and $R^2$ denotes an alkyl group having up to 3 C atoms; with the proviso that one of the groups $R^1$ and $R^3$ represents such an aforedefined dihydroxy- or hydroxyalkyl group or that $R^3$ represents the aforedefined oxoalkyl group. A further preferred embodiment of the invention relates to therapeutic agents which contain at least one of those compounds of the formula I in which $R^1$ denotes straight or branched chain $(C_2-C_5)$alkyl or allyl; $R^2$ represents methyl or ethyl; and $R^3$ is 5,6-dihydroxyhexyl, 6,7-dihydroxyheptyl, 4,5-dihydroxyhexyl, or 5-hydroxyhexyl. Among these therapeutic agents, those in turn are particularly preferred which contain at least one of those compounds of the formula I in which $R^1$ represents propyl, isopropyl, butyl, isobutyl, or allyl; $R^2$ is methyl or ethyl; and $R^3$ denotes the 5,6-dihydroxyhexyl radical. The therapeutic agents are prepared by bringing at least one compound of the formula I—advantageously together with at least one usual carrier and/or excipient—into a suitable form for administration.

The invention also relates to novel trisubstituted xanthine derivatives of the formula I, in which $R^2$ is $(C_1-C_4)$alkyl and either $R^3$ denotes 5,6-dihydroxyhexyl, 5-hydroxyhexyl, or 5-oxohexyl whilst $R^1$ represents alkenyl, ($\omega$-1)-hydroxyalkyl, or ($\omega$-1)-oxoalkyl having each 3 to 6 C atoms or $R^1$ denotes 5-hydroxyhexyl, 5,6-dihydroxyhexyl, or 4,5-dihydroxyhexyl whilst $R^3$ represents allyl, 2-hydroxypropyl, or 2-oxopropyl. In this context, particularly suitable compounds are those in which $R^1$ represents alkenyl, ($\omega$-1)-hydroxyalkyl, or ($\omega$-1)-oxoalkyl having each 3 to 6 C atoms, $R^2$ is $(C_1-C_4)$alkyl, and $R^3$ denotes 5,6-dihydroxyhexyl. Among the compounds mentioned latterly, the 1-alkenyl-3-alkyl-7-(5,6-dihydroxyhexyl)-xanthines having 3 to 6 C atoms in the alkenyl group $R^1$ and 1 to 4 C atoms in the alkyl group $R^2$, such as, for example, 1-allyl-3-ethyl-7-(5,6-dihydroxyhexyl)-xanthine, in turn represent particularly preferred compounds according to formula I.

Pentoxifylline, the compound of the general formula I wherein $R^1$ is 5-oxohexyl and $R^2$ and $R^3$ are methyl, has already been reported by Vorobyev and Samsonov to have antiulcer effects (Ter. Arkh. 57, 52–55, 1985). However, the efficacy is not high enough to be a promising drug for pectic ulcer disease. The compounds involved in this invention have been shown, as described below, to be much more effective than pentoxifylline and to have low toxicity, indicating that they are effective antiulcer drugs producing a low incidence of side effects.

Some of the compounds used as active ingredients in this invention are described in Japanese laid open Patent Publication (JP-LOP) 67687/83 (corresponding to European Patent 75 850 or also to U.S. Pat. Nos. 4,616,020 and 4,713,455). The novel compounds are prepared by routine methods from known compounds in analogy to the methods described, for example in the before-mentioned JP-LOP or also in the international application published under the Patent Cooperation Treaty WO 87/00523. A convenient method is the introduction of $R^1$ or $R^3$ by alkylation. The alkylation is carried out by reacting a compound of the general formula I wherein $R^1$ or $R^3$ is hydrogen with an alkylating agent such as $R^1$-halogen or $R^3$-halogen under alkaline conditions. Compounds in which $R^1$ and/or $R^3$ is hydroxyalkyl can also be produced by reduction of the corresponding oxoalkyl compounds.

Somewhat more detailed, the novel trisubstituted xanthine derivatives of the formula I, in which $R^2$ is $(C_1-C_4)$alkyl, and either $R^3$ denotes 5,6-dihydroxyhexyl, 5-hydroxyhexyl or 5-oxohexyl whilst $R^1$ represents alkenyl, $(\omega-1)$-hydroxyalkyl or $(\omega-1)$-oxoalkyl having each 3 to 6 C atoms or $R^1$ denotes 5-hydroxyhexyl, 5,6-dihydroxyhexyl or 4,5-dihydroxyhexyl whilst $R^3$ represents allyl, 2-hydroxypropyl or 2-oxopropyl, are conveniently prepared a) by reacting a 3-alkylxanthine of the formula II

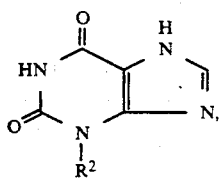

in which $R^2$ has the meaning as defined above, if desired in the presence of a basic agent or in the form of a salt, with an alkylating agent of the formula $R^3$—X, in which X is halogen or a sulfonic acid ester or phosphoric acid ester group and $R^3$ has the meaning as defined above, to yield a compound of the formula III

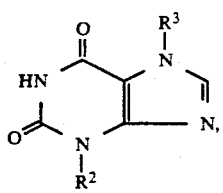

which, again preferably in the presence of a base or in form of a salt, is then alkylated with the alkylating agent $R^1$—X, in which X and $R^1$ have the meaning as defined above, to give a compound of the formula I, whereby the introduction of the dihydroxyhexyl groups can also conveniently be performed by using the alkylating agents $R^1$—X or $R^3$—X in the isopropylidene-protected form of the formula

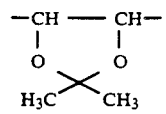

and subsequent hydrolytical opening of the 1,3-dioxolane ring with splitting off of acetone, or b) by reducing a compound of the formula I, in which $R^1$ and/or $R^3$ is an oxoalkyl group, by a conventional reducing agent at the keto group to the corresponding hydroxyalkylated xanthine of the formula I.

Process variant a:

The reaction of the mono- and disubstituted xanthine derivatives II or III, respectively, with the alkylating agents is usually carried out in a dispersing agent or solvent which is inert towards the participants in the reaction. Possible dispersing agents or solvents are, in particular, dipolar aprotic solvents, for example formamide, dimethylformamide, dimethylacetamide, N-methylpyrrolidone, tetramethylurea, hexamethylphosphoric acid triamide, dimethyl sulfoxide, acetone and butanone; however, it is also possible to use alcohols, such as methanol, ethylene glycol and mono- or dialkyl ethers thereof, in which the alkyl group has 1 to 4 carbon atoms but both together have not more than 5 carbon atoms, ethanol, propanol, isopropanol and the various butanols; hydrocarbons, such as benzene, toluene or xylenes; halogenated hydrocarbons, such as methylene chloride or chloroform; pyridine and mixtures of the solvents mentioned or mixtures thereof with water.

The alkylation reactions are advantageously carried out in the presence of a basic condensing agent. Agents which are suitable for this are, for example, alkali metal or alkaline earth metal hydroxides, carbonates, hydrides and alcoholates, and organic bases such as trialkylamines (for example triethyl- or tributylamine), quaternary ammonium or phosphonium hydroxides and cross-linked resins with fixed, optionally substituted ammonium or phosphonium groups. However, the xanthine derivatives can also be employed in the alkylation reaction directly in the form of their separately prepared salts, for example the alkali metal, alkaline earth metal or optionally substituted ammonium or phosphonium salts. The mono- and disubstituted xanthine compounds can moreover be conveniently alkylated both in the presence of the abovementioned inorganic condensing agents and in the form of their alkali metal or alkaline earth metal salts with the aid of so-called phase transfer catalysts, for example tertiary amines, quaternary ammonium or phosphonium salts or crown ethers, preferably in a two-phase system under the conditions of phase transfer catalysis. Suitable phase transfer catalysts, which are mostly commercially available, are, inter alia, tetra$(C_1-C_4)$-alkyl- and methyltrioctylammonium and -phosphonium salts, methyl-, myristyl-, phenyl- and benzyltric$(C_1-C_4)$alkyl- and cetyltrimethylammonium salts and $(C_1-C_{12})$alkyl- and benzyl-triphenylphosphonium salts, as a rule those compounds which have the cation which is larger and of more symmetric structure proving to be more effective.

The introduction of the radicals $R^1$ and $R^3$ by the procedures described above is in general carried out at a reaction temperature between 0° C. and the boiling point of the particular reaction medium used, preferably between 20° C. and 130° C., if appropriate under increased or reduced pressure, but usually under atmospheric pressure, it being possible for the reaction time to be from less than one hour to several hours.

For the conversion of the 3-alkylxanthines II into the compounds of the formula I with two equal radicals $R^1$ and $R^3$ (=5-hydroxyhexyl or 5-oxohexyl), it is possible to carry out the alkylation in a one-pot reaction, without isolation of intermediate products.

Process variant b:

The reduction of the xanthines of the formula I carrying an oxoalkyl group in the position of $R^1$ and/or $R^3$ to the corresponding hydroxyalkyl compounds can in principle be carried out both with base metals and by catalytic hydrogenation, but the method of choice comprises reaction with simple metal hydrides ($MH_n$), complex metal hydrides ($M^1[M^2H_n]_m$) or organometallic hydrides (Houben-Weyl, volume IV/1 d (1981), pages 267-282, and volume VI/1 b (1984), pages 141-155), which proceeds under very mild conditions and with high yields. Of the numerous complex metal hydrides which can be used for reduction of ketones, the reagents most frequently used may be mentioned as examples, that is to say lithium alanate, lithium boranate and, in particular, sodium boranate, which is easier to handle because of its lower reactivity and in particular allows the reaction to be carried out in alcoholic, alcoholic-aqueous or purely aqueous solutions or suspensions. Nitriles, such as acetonitrile, can also be used as the reaction medium, as well as the otherwise customary inert solvents, such as ethers (for example diethyl ether, tetrahydrofuran or 1,2-dimethoxyethane), hydrocarbons and pyridine. The hydrogenation, which is advantageously carried out at temperatures between 0° C. and the boiling point of the particular solvent, but preferably at room temperature, as a rule proceeds rapidly and ends within some minutes to a few hours.

Possible administration routes of the compounds involved in this invention are oral, intravenous, subcutaneous, intramuscular, and rectal. The clinical dose is 100–900 mg/60 kg body weight, preferably 300–600 mg/60 kg body weight. Usable dosage forms are tablets, sugar-coated tablets, pills, capsules, powders, granules, suppositories, and injections. The tablets, sugar-coated tablets, capsules, and granules are desirable for oral, the injections for parenteral, and the suppositories for rectal administration.

The compounds involved in this invention can be used each as a monopharmacon or as a combination or in combination with other agents for the treatment of peptic ulcer disease including antacids.

For injection, the powder for injection is usable. In this case, the compounds involved in this invention are dissolved in water containing one or more adequate water-soluble excipients such as mannitol, sucrose, lactose, maltose, glucose, and fructose. Then the solution is put into the vial or ampoule which is sealed after lyophilization of the contents.

For oral administration, an enteric-coated preparation is possible in addition to the dosage forms listed above. In this case, the tablets, granules, or fine granules are prepared using the following as additives as required: excipients such as mannitol, sucrose, lactose, maltose, starch, silica, and calcium phosphate; lubricants such as talc and magnesium stearate; binders such as sodium carboxymethylcellulose, methylcellulose, gelatin, and gum arabic; and disintegrating aids such as calcium carboxymethylcellulose. Then, the tablets, granules, or fine granules are coated with one or more enteric bases with, if required, a coloring agent such as titanium dioxide. The bases for enteric coating include cellulose acetate phthalate, hydroxypropylmethylcellulose phthalate, hydroxypropylmethylcellulose acetylsuccinate, polyvinyl alcohol phthalate, styrene-maleic anhydride copolymers, styrene-maleic acid copolymers, methyl methacrylatemethacrylic acid copolymers, and methyl acrylate-methacrylic acid copolymers. The enteric-coated granules or fine granules are preferably filled into capsules.

Enteric-coated capsules can be obtained by coating capsules manufactured by a conventional method with one or more of the enteric bases listed above or by manufacturing capsules with an enteric base alone or in admixture with gelatin.

Suppositories can be prepared as follows. The compounds involved in this invention are mixed homogenously with (a) lipophilic base such as cacao butter or adeps solidus in various proportions or (b) a hydrophilic base such as polyethylene glycol or glycerol. The mixture containing the compounds of this invention is put into molds.

The weight ratio of the active ingredient(s) of the formula I (known and novel compounds) and the respective carrier or excipient can vary within a very wide range; preferably it is within the range of about 1:100 to about 100:1.

The antiulcer effects and the toxicological profile of the compounds involved in this invention were as follows. The compounds tested are shown in Table 1. Pentoxifylline, 1,2,3,6-tetrahydro-3,7-dimethyl-1-(5-oxohexyl)-purine-2,6-dione, was used as a reference drug for the pharmacological studies.

TABLE 1

Compounds of formula I (known and novel)

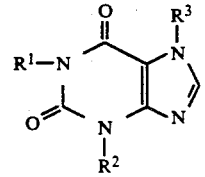
(I)

| Compound No. | $R^1$ | $R^2$ | $R^3$ |
|---|---|---|---|
| 1 | $CH_3-(CH_2)_2-$ | $-C_2H_5$ | $-(CH_2)_4-CH-CH_2$ <br> $\phantom{-(CH_2)_4-}|\phantom{CH}|$ <br> $\phantom{-(CH_2)_4-}OH\phantom{C}OH$ |

TABLE 1-continued

Compounds of formula I (known and novel)

$$\text{(I)}$$

Structure: R¹-N attached to a fused bicyclic system (pyrimidine-imidazole) with two C=O groups, R² on one N, R³ on imidazole N.

| Compound No. | R¹ | R² | R³ |
|---|---|---|---|
| 2 | $CH_3-CH(CH_3)-$ | " | " |
| 3 | $CH_3-(CH_2)_3-$ | " | " |
| 4 | $CH_3-(CH_2)_4-$ | " | " |
| 5 | $CH_3-CH(CH_3)-CH_2-$ | " | " |
| 6 | $CH_2=CH-CH_2-$ | " | " |
| 7 | $CH_3-C(=O)-CH_2-$ | " | " |
| 8 | $CH_3-CH(OH)-CH_2-$ | " | " |
| 9 | $CH_3-C(=O)-(CH_2)_4-$ | $-C_3H_7$ | " |
| 10 | $CH_3-(CH_2)_3-$ | $-CH_3$ | " |
| 11 | $CH_3-C(=O)-(CH_2)_4-$ | " | " |
| 12 | $CH_3-(CH_2)_2-$ | $-C_2H_5$ | $-(CH_2)_3-CH(OH)-CH(OH)-CH_3$ |
| 13 | $CH_3-(CH_2)_2-$ | " | $-(CH_2)_5-CH(OH)-CH_2-OH$ |
| 14 | $CH_2(OH)-CH(OH)-(CH_2)_4-$ | " | $-(CH_2)_2-CH_3$ |
| 15 | $CH_3-(CH_2)_2-$ | $-CH_3$ | $-(CH_2)_4-CH(OH)-CH_3$ |
| 16 | $CH_3-(CH_2)_3-$ | " | " |
| 17 | $CH_3-(CH_2)_5-$ | " | " |
| 18 | $CH_2=CH-CH_2-$ | " | " |
| 19 | $CH_3-C(=O)-CH_2-$ | " | " |
| 20 | $CH_3-C(=O)-(CH_2)_4-$ | " | $-CH_2-CH(OH)-CH_3$ |
| 21 | $CH_3-CH(OH)-(CH_2)_4-$ | " | $-CH_2-CH=CH_2$ |
| 22 | $C_2H_5-$ | " | $-(CH_2)_4-C(=O)-CH_3$ |

TABLE 1-continued

Compounds of formula I (known and novel)

$$\text{(I)}$$

(structure showing R¹-N, R³-N, R²-N substituted bicyclic with C=O groups)

| Compound No. | R¹ | R² | R³ |
|---|---|---|---|
| 23 | CH₃—CH(OH)—(CH₂)₄— | " | —CH₂—C(=O)—CH₃ |
| 24 | CH₃—C(=O)—CH₂— | " | —(CH₂)₄—C(=O)—CH₃ |
| 25[a] | CH₃—C(=O)—(CH₂)₄— | " | —CH₃ |

[a]Reference compound (pentoxifylline)

1. ANTIULCER EFFECTS

1.1 Protective Effect on Gastric Ulcer Induced by Restraint Plus Water-Immersion Stress in Rats Male Sprague-Dawley rats weighing 250-300 g were used in groups of 5-34. The animals were given the compounds by the oral route after fasting overnight. Immediately, under light ether anesthesia they were placed in a restraint box and immersed in water at 20° C. for 6 or 7 hours. Then the animals were sacrificed, and their stomachs were isolated, inflated with 4 ml of 1% formalin for 10 minutes, opened along the greater curvature, and examined for the presence of gastric erosions. The longest axis of each erosion induced on the glandular section of the stomach was measured, and the sum of the lengths was defined as an ulcer index. The results are shown in Table 2.

TABLE 2

Protective effect on stress-induced gastric ulcer in rats

| Compound | Dose (mg/kg, po) | No. of animals | Ulcer index (mm) | Inhibition (%) |
|---|---|---|---|---|
| Control (Distilled water) | 0 | 24 | 19.7 ± 2.9 | — |
| 1 | 10 | 5 | 2.7 ± 0.9** | 86.3 |
| 3 | 10 | 5 | 6.0 ± 1.9** | 69.6 |
| 15 | 10 | 5 | 2.2 ± 0.9** | 88.9 |
| 18 | 10 | 5 | 15.3 ± 2.1 | 22.3 |
| 20 | 10 | 5 | 6.9 ± 2.1* | 65.0 |
| 22 | 10 | 5 | 8.0 ± 4.2 | 59.0 |
| 23 | 10 | 5 | 15.8 ± 4.6 | 19.8 |
| 24 | 10 | 5 | 10.3 ± 3.5 | 47.7 |
| 25[a] | 10 | 5 | 17.2 ± 5.6 | 12.7 |
| Control (Distilled water) | 0 | 34 | 26.2 ± 1.6 | — |
| 2 | 10 | 5 | 11.5 ± 2.1** | 56.0 |
| 4 | 10 | 5 | 9.2 ± 1.9** | 64.7 |
| 5 | 10 | 5 | 7.1 ± 1.8** | 72.9 |
| 6 | 10 | 5 | 7.0 ± 0.9** | 73.2 |
| 7 | 10 | 5 | 20.4 ± 4.1* | 21.9 |
| 8 | 10 | 5 | 20.7 ± 4.6 | 21.0 |
| 9 | 10 | 5 | 20.2 ± 5.8 | 22.9 |
| 10 | 10 | 5 | 4.5 ± 1.4** | 82.8 |
| 11 | 10 | 6 | 13.8 ± 1.7* | 47.4 |
| 12 | 10 | 5 | 4.3 ± 0.8** | 83.5 |
| 13 | 10 | 5 | 8.9 ± 2.1* | 66.0 |
| 14 | 10 | 5 | 10.4 ± 1.9** | 60.2 |
| 16 | 10 | 5 | 10.6 ± 0.9** | 59.4 |
| 19 | 10 | 5 | 15.0 ± 2.4* | 42.8 |

TABLE 2-continued

Protective effect on stress-induced gastric ulcer in rats

| Compound | Dose (mg/kg, po) | No. of animals | Ulcer index (mm) | Inhibition (%) |
|---|---|---|---|---|
| 21 | 10 | 5 | 13.4 ± 3.2** | 48.9 |

[a]Reference compound (pentoxifylline)
**$p < 0.01$,
*$p < 0.05$
Each value represents the mean ± S.E.

1.2 Protective Effect on Ethanol-Induced Gastric Ulcer in Rats

Male Sprague-Dawley rats weighing 250-300 g were used in groups of 5-24. After fasting overnight, the animals were given orally the compounds. Thirty minutes later they received absolute ethanol (1 ml/body) orally and were sacrificed after 60 minutes. The stomach was removed and examined for erosions. The ulcer index was obtained in the same way as under 1.1. The results are shown in Table 3.

TABLE 3

Protective effect on ethanol-induced gastric ulcer in rats

| Compound | Dose (mg/kg, po) | No. of animals | Ulcer index (mm) | Inhibition (%) |
|---|---|---|---|---|
| Control (Distilled water) | 0 | 24 | 111.6 ± 10.4 | — |
| 2 | 10 | 5 | 6.7 ± 2.8** | 94.0 |
| 4 | 10 | 5 | 15.6 ± 5.8** | 86.0 |
| 6 | 10 | 5 | 10.7 ± 1.4** | 90.4 |
| 10 | 10 | 5 | 1.1 ± 0.5** | 99.0 |
| 13 | 10 | 5 | 5.0 ± 2.2** | 95.5 |
| 16 | 10 | 5 | 4.1 ± 0.8** | 96.3 |
| Control (Distilled water) | 0 | 21 | 164.7 ± 19.4 | — |
| 1 | 10 | 5 | 6.7 ± 2.1** | 95.8 |
| 3 | 10 | 5 | 5.3 ± 3.3** | 96.8 |
| 25[a] | 10 | 5 | 34.9 ± 10.9** | 78.8 |
| Control (10% EtOH) | 0 | 13 | 118.8 ± 9.6 | — |
| 17 | 10 | 5 | 13.4 ± 5.2** | 88.7 |

[a]Reference compound (pentoxyfylline)
**$p < 0.01$
Each value represents the means ± S.E.

2. TOXICOLOGICAL PROFILE

LD$_{50}$ values of the compounds of this invention were determined after intravenous injection or intraperitoneal administration to mice for acute toxicity test. The studies were carried out using male and female NMRI mice (n=3/group) having a body weight between 19-21 g. The test substance was dissolved in double distilled water or suspended in 1% carboxymethyl cellulose sodium for administration, and the animals were observed for 7 days. The results are shown in Table 4.

TABLE 4

Acute intravenous or intraperitoneal toxicity of the compounds involved in this invention in mice

| Compound | LD$_{50}$ (mg/kg) |
|---|---|
| 1 | 254.0$^a$ |
| 4 | >200.0 |
| 5 | >200.0 |
| 6 | >200.0 |
| 7 | >200.0 |
| 8 | >200.0 |
| 9 | >200.0 |
| 10 | 147.0$^a$ |
| 11 | >200.0 |
| 12 | >200.0 |
| 13 | 200.0–400.0 |
| 14 | 300.0–600.0$^b$ |
| 15 | 123.0$^a$ |
| 16 | 100.0–200.0 |
| 17 | 500.0–1000.0$^b$ |
| 18 | 250.0–500.0$^b$ |
| 19 | >200.0 |
| 20 | >200.0 |
| 21 | 100.0–200.0 |
| 22 | 200.0–400.0$^b$ |
| 23 | >200.0 |
| 24 | >200.0 |
| 25 | 209.0$^a$ |

$^a$LD$_{50}$ values were obtained by the method of Litchfield-Wilcoxon using 10 mice/dose.
$^b$Intraperitoneal administration Examples of the invention will be as follows.

A) PREPARATION EXAMPLES (FOR THE NOVEL COMPOUNDS OF FORMULA I)

1) Production of 7-(5,6-dihydroxyhexyl)-3-methyl-1-(5-oxohexyl)-xanthine (Compound 11)

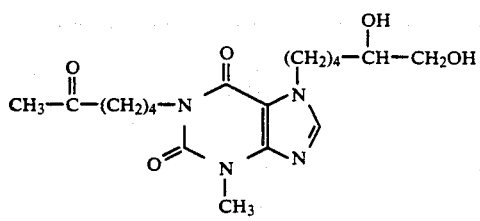

29.6 g of 7-(5,6-isopropylidenedioxyhexyl)-3-methylxanthine, 13 g of potassium carbonate, and 12.8 g of 1-chlorohexan-5-one in 140 ml of dimethylformamide were stirred for 8 hours at an internal temperature of 120° C. After removal of the solvent under reduced pressure, the residue was taken up with methylene chloride and washed with dilute sodium hydroxide solution and the neutralized and dried methylene chloride phase was evaporated. The residue was heated in 400 ml of sulfuric acid at a pH of 0.5 for 2 hours at 100° C. After cooling down, the mixture was neutralized with dilute sodium hydroxide solution and evaporated under reduced pressure, the residue was taken up with methylene chloride, and the resulting mixture was washed with dilute sodium hydroxide solution and with water, dried and evaporated under reduced pressure. The crude product was purified by column-chromatography on silica gel (mobile phase: methylene chloride/ethanol, volume ratio 8:3) and subsequent recrystallization from methylene chloride/diethylether.

Yield: 19.3 g (55.3% of theory). melting point: 93°-94° C. $C_{18}H_{28}N_4O_5$ (MW=380.45).

Analysis: calculated: C, 56.83%; H, 7.42%; N, 14.73%. Found: C, 57.06%; H, 7.39%; N, 14.75%.

2) Production of 7-allyl-1-(5-hydroxyhexyl)-3-methylxanthine (Compound 21)

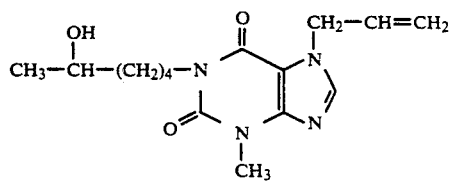

To 11.8 g of 7-allyl-3-methyl-1-(5-oxyhexyl)-xanthine (prepared by alkylation of 7-allyl-3-methylxanthine with 1-chlorohexan-5-one in dimethylformamide in the presence of potassium carbonate at 100° C. for 5 hours; melting point: 71° C.), dissolved in 200 ml of ethanol, 1.5 g of sodium borohydride was added slowly under stirring at a temperature of max. 30° C. After stirring at room temperature for 6 hours the mixture was evaporated under reduced pressure. The residue was extractively worked up with dilute sodium hydroxide solution and with methylene chloride. The combined methylene chloride phases were washed with water, dried and evaporated under reduced pressure. The residue was purified by means of chromatography on silica gel (mobile phase: methylene chloride/ethanol/ammonia-solution (28%), volume ratio 8:2:0.2) and by recrystallization from methylene chloride/diethylether.

Yield: 7.8 g (65.5% of theory). melting point: 86° C. $C_{15}H_{22}N_4O_3$ (MW=306.37).

Analysis: calculated: C, 58.81%; H, 7.24%; N,18.29%. Found: C, 58.99%; H, 7.38%; N, 18.39%.

In an analogous manner to Example 1 or 2 the following compounds were obtained:

3) 1-Allyl-3-ethyl-7-(5,6-dihydroxyhexyl)-xanthine (Compound 6)

This compound was prepared as described in Example 1, starting from 20.2 g of 3-ethyl-7-(5,6-isopropylidenedioxyhexyl)-xanthine and 7.5 g of allyl bromide.

Yield: 10.5 g (52% of theory). melting point: 91° C. $C_{16}H_{24}N_4O_4$ (MW=336.39).

Analysis: calculated: C, 57.13%; H, 7.19%; N, 16.66%. Found: C, 57.02%; H, 7.2%; N, 16.62%.

4) 3-Ethyl-7-(5,6-dihydroxyhexyl)-1-(2-oxopropyl)-xanthine (Compound 7)

This compound was prepared starting from 3-ethyl-7-(5,6-isopropylidenedioxyhexyl)-xanthine and chloroacetone according to the procedure described in Example 1.

$C_{16}H_{24}N_4O_5$ (MW=352.39).

Melting point: 101°–103° C.

5) 3-Ethyl-7-(5,6-dihydroxyhexyl)-1-(2-hydroxypropyl)-xanthine (Compound 8)

This compound was prepared starting from Compound 7 by reduction of the oxopropyl group according to the method described in Example 2, or by alkylation of 3-ethyl-7-(5,6-isopropylidenedioxyhexyl)-xanthine with 1-chloro-propan-2-ol according to the procedure as described in Example 1.

$C_{16}H_{26}N_4O_5$ (MW=354.41).

Melting point: 118°–123° C.

6) 7-(5,6-Dihydroxyhexyl)-1-(5-oxohexyl)-3-n-propylxanthine (Compound 9)

This compound was prepared according to Example 1, starting from 41.5 g of 7-(5,6-isopropylidenedioxyhexyl)-3-propylxanthine and 16.8 g of 1-chlorohexan-5-one.

Yield: 29.5 g (61% of theory). melting point: 80°–82° C. $C_{20}H_{32}N_4O_5$ (MW=408.50).

Analysis: calculated: C, 58.8%; H, 7.9%; N 13.72%. Found: C, 58.71%; H, 7.81%; N 13.85%.

7) 1-Allyl-7-(5-hydroxyhexyl)-3-methylxanthine (Compound 18)

This compound was prepared starting from 7-(5-hydroxyhexyl)-3-methylxanthine by alkylation with allyl bromide in dimethylformamide in the presence of potassium carbonate as described in Example 1; however, without the treatment with sulfuric acid.

$C_{15}H_{22}N_4O_3$ (MW=306.37).

Melting point: 57°–58° C.

8) 7-(5-Hydroxyhexyl)-3-methyl-1-(2-oxopropyl)-xanthine (Compound 19)

This compound was prepared by alkylation of 7-(5-hydroxyhexyl)-3-methylxanthine with chloroacetone according to the method described in Example 1; however, without the sulfuric acid treatment.

$C_{15}H_{22}N_4O_4$ (MW=322.37).

Melting point: 97°–98° C.

9) 1-(5-Hydroxyhexyl)-3-methyl-7-(2-oxopropyl)-xanthine (Compound 23)

This compound was prepared starting from 3-methyl-7-(2-oxopropyl)-xanthine by alkylation with 1-chlorohexan-5-ol as described in Example 1; however, without the sulfuric acid treatment.

$C_{15}H_{22}N_4O_4$ (MW=322.37).

Melting point: 139°–141° C.

10) 3-Methyl-7-(5-oxohexyl)-1-(2-oxopropyl)-xanthine (Compound 24)

This compound was prepared by alkylation of 3-methyl-7-(5-oxohexyl)-xanthine with chloroacetone in dimethylformamide in the presence of potassium carbonate at 100° C. for 1.5 hours.

$C_{15}H_{20}N_4O_4$ (MW=320.35).

Melting point: 105°–106° C.

B) THERAPEUTIC AGENTS

1) An injectable preparation was prepared as follows. Compound 1 (20 g) and sodium chloride (16 g) were added to distilled water for injection to make 2000 ml. The solution was filtered through a 0.22 μm Millipore filter and divided at 5 ml into 5-ml ampoules, which were sealed and sterilized in an autoclave.

2) Tablets each containing 115 mg of Compound 1 were prepared by a conventional method from a mixture of 500 g of Compound 1 with 250 g of lactose, 150 g of corn starch, 150 g of calcium carboxymethylcellulose, 42 g of talc, 5 g of magnesium stearate, and 3 g of silica. The tablets were coated with a suspension containing 500 ml of water, 40 g of hydroxypropylmethylcellulose, 2 g of polyethyleneglycol with the average molecular weight of 6000, 3.5 g of titanium dioxide and 3 g of talc.

EFFECTS OF THE INVENTION

As revealed by our studies described above, the compounds involved in this invention were shown to possess potent antiulcer effects and low toxicity. For example, Compound 1 is (a) 6 to 7 times more effective than Comparison Compound 25 in improving stress-induced gastric ulcers and has (b) low toxicity. The compounds involved in this invention other than Compound 1 also have more potent antiulcer effects than Compound 25.

What is claimed is:

1. A compound of the formula I in which $R^2$ is $(C_1–C_4)$alkyl, $R^3$ is 5,6-dihydroxyhexyl or 5-hydroxyhexyl, and $R^1$ is alkenyl having 3 to 6 C-atoms.

2. A compound of the formula I as claimed in claim 1 in which $R^3$ is 5,6-dihydroxyhexyl.

3. A compound of the formula I as claimed in claim 1 in which $R^2$ is $(C_1–C_2)$alkyl.

4. A compound of the formula I as claimed in claim 1, which represents 1-allyl-3-ethyl-7-(5,6-dihydroxyhexyl)xanthine.

5. A method for the treatment of a patient suffering from peptic ulcer disease, inclusive of irritations of the gastro-intestinal mucosa produced by drugs, which comprises administering to said patient an effective amount of at least one compound of the formula I wherein $R^1$ is $(C_1–C_8)$alkyl or $(C_3–C_6)$alkenyl, $R^3$ is $$-(CH_2)_m-\underset{OH}{CH}-\underset{OH}{CH}-R^4 \quad \text{or} \quad -(CH_2)_n-\underset{OH}{CH}-R^5,$$

and $R^2$ is $(C_1–C_4)$alkyl; $R^4$ and $R^5$ are each hydrogen or $(C_1–C_2)$alkyl; and m and n are each 1, 2, 3, 4, 5 or 6.

6. The method as claimed in claim 5 wherein, in the compound of the formula I, $R^1$ is a straight-chain or branched alkyl group having up to 6 C-atoms or allyl, $R^3$ is ($\omega$, $\omega$-1)- or ($\omega$-1, $\omega$-2)-dihydroxyalkyl having 4 to 7 C-atoms or ($\omega$-1)-hydroxy-alkyl having 3 to 6 C-atoms,

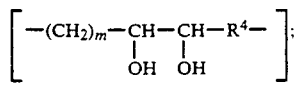

and $R^2$ is an alkyl group having up to 3 C-atoms.

7. The method as claimed in claim 5 wherein, in the compound of the formula I, $R^1$ is straight or branched chain ($C_2$-$C_5$)alkyl or allyl; $R^2$ is methyl or ethyl; and $R^3$ is 5,6-dihydroxyhexyl, 6,7-dihydroxyheptyl, 4,5-dihydroxyhexyl or 5-hydroxyhexyl.

8. The method as claimed in claim 5 wherein, in the compound of the formula I, $R^1$ is propyl, isopropyl, butyl, isobutyl or allyl; $R^2$ is methyl or ethyl; and $R^3$ is 5,6-dihydroxyhexyl.

* * * * *

UNITED STATES PATENT AND TRADEMARK OFFICE
CERTIFICATE OF CORRECTION

PATENT NO.   : 5,082,845
DATED        : January 21, 1992
INVENTOR(S)  : Erhard Wolf et al.

It is certified that error appears in the above-indentified patent and that said Letters Patent is hereby corrected as shown below:

Claim 6, column 16, line 1, the formula

" 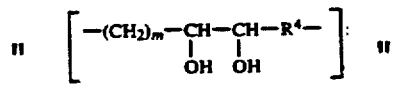 "

should be deleted.

Signed and Sealed this

Sixth Day of September, 1994

Attest:

Attesting Officer

BRUCE LEHMAN
Commissioner of Patents and Trademarks